United States Patent [19]

Spada et al.

[11] Patent Number: 4,906,629
[45] Date of Patent: Mar. 6, 1990

[54] PYRIDAZINONE AND PYRAZOLONE COMPOUNDS, CARDIOTONIC COMPOSITIONS INCLUDING SAME, AND THEIR USES

[75] Inventors: Alfred P. Spada, Ambler; William L. Studt, Harleysville; Henry F. Campbell, North Wales; Donald E. Kuhla, Doylestown; Thomas Tucker, North Wales, all of Pa.

[73] Assignee: Rorer Pharmaceutical Corporation, Fort Washington, Pa.

[21] Appl. No.: 255,749

[22] Filed: Oct. 11, 1988

Related U.S. Application Data

[63] Continuation-in-part of Ser. No. 47,395, May 8, 1987, Pat. No. 4,829,066, which is a continuation-in-part of PCT US88/01527 filed May 4, 1988.

[51] Int. Cl.$^4$ .................... A61K 31/50; C07D 498/04
[52] U.S. Cl. ..................................... 514/254; 544/238
[58] Field of Search ......................... 544/238; 514/254

[56] References Cited

U.S. PATENT DOCUMENTS 3,854,926 12/1974 Senkbeil .......................... 544/105 X
3,984,405 10/1976 Krapcho ............................. 544/105
4,725,686 2/1988 Kuhla et al. ........................ 544/238

Primary Examiner—Richard L. Raymond
Attorney, Agent, or Firm—Martin F. Savitzky; James A. Nicholson; Alexis Barron

[57] ABSTRACT

This invention relates to substituted pyridooxazinone and naphtheridone pyridazinone and pyrazolone compounds which are useful as cardiotonic agents for the treatment of congestive heart failure, to methods for increasing cardiac contractility using said compounds, and pharmaceutical compositions including the same.

20 Claims, No Drawings

PYRIDAZINONE AND PYRAZOLONE COMPOUNDS, CARDIOTONIC COMPOSITIONS INCLUDING SAME, AND THEIR USES

This is a continuation-in-part of U.S. Ser. No. 47,395, filed May 8, 1987, now U.S. Pat. No. 4,829,066, and PCT/US88/01527, filed May 4, 1988.

FIELD OF INVENTION

This invention relates to diazabicyclic substituted pyridazinone and pyrazolone compounds which are useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Cardiotonic agents which are described as having positive inotropic activity include the 5-pyridyl substituted pyridones disclosed in U.S. Pat. Nos.: 4,004,012; 4,072,746; 4,137,233; 4,199,586; 4,271,168 and 4,107,315; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572, cardiotonic pyridyl substituted carbostyril compounds disclosed in EPO application Serial No. 84308925.1, and the 5-substituted-1,6-naphthyridine-2(1H)one compounds disclosed in U.S. Pat. No. 4,657,915.

Cardiotonic bicyclic heteroaryl-5-substituted pyridyl compounds are disclosed in PCT published application Ser. No. PCT/US83/01285; and, cardiotonic diazheterocyclic-5-substituted pyridyls are disclosed in U.S. Pat. Nos. 4,432,979, 4,514,400 and 4,539,321. Each of the aforementioned is owned by the same assignee as the present application.

Cardiotonic 4,5-dihydro-5-[4-(H-imidazol-1-yl)phenyl]-3(2)-pyridazinones are disclosed in Bristol et al., J. Med. Chem. 22, 1099 (1984); cardiotonic imidazolyl substituted pyridazinones are disclosed in U.S. Pat. No. 4,521,416, cardiotonic benzodiazinone substituted pyridazinones and pyrazolyls are disclosed in U.S. Pat. No. 4,725,686, and cardiotonic benzothiazolone substituted pyridazinones are disclosed in published EPO Patent Appl. Ser. No. 84108656.4 (Publ. No. 0132817). Cardiotonic compounds including a pyrazole group are disclosed in published EPO Patent Appl. Ser. No. 84303456.2 (publ. No. 0126651) and U.S. Pat. Nos. 4,526,895 and 4,526,982.

SUMMARY OF THE INVENTION

The present invention relates to naphtheridone- and pyridooxazinone-pyridazinone and pyrazolone compounds which are useful for increasing cardiac contractility in humans and other mammals.

The compounds of the present invention include compounds of Formula I:

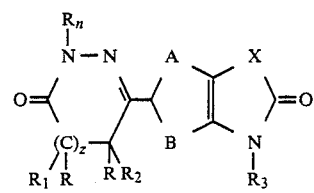

wherein:

A is —C= or —N=;

B is —C=C—, —C= N— or —N=C—;

provided that A or B represents a nitrogen-containing group;

X is —$(CR_4R_5)_a$—$(O)_b$—$(CR_6R_7)_c$—;

a and c are 0, 1 or 2;

b and z are 0 or 1;

provided that a+b+c=1, 2 or 3;

$R_n$ is hydrogen, alkyl, aralkyl, aryl, acyl, carbalkoxy, carbamyl, carbalkoxyalkyl, hydroxyalkyl, alkoxyalkyl, or amidino;

R, $R_1$, $R_2$, $R_3$, $R_5$ and $R_6$ are hydrogen, alkyl, or aralkyl;

$R_4$ is hydrogen, alkyl, aryl, or aralkyl;

$R_7$ is hydrogen, alkyl, aralkyl, aryl, acyl, carbalkoxy, carbalkoxyalkyl, hydroxyalkyl, alkoxyalkyl, amidino, alkoxy, amino, nitro, carboxy, cyano, alkyl amino, halo, hydroxy, mercaptyl, alkyl mercaptyl, carboalkyl or carbamoyl;

R and $R_6$ groups on vicinal carbon atoms may together form a carbon-carbon double bond provided that R groups require $R_n$ to be hydrogen and z=1;

$R_6$ and $R_7$ geminal groups may together form a spiro substituent, —$(CH_2)_d$—, where d is 2 to 5;

$R_2$ is hydrogen or —$(CH_2)_y$—Y where y is 1-3;

Y is hydrogen, —O—$R_\alpha$, —S—$R_\alpha$ or —$NR_\alpha R_\beta$;

$R_\alpha$ is hydrogen, alkyl or acyl;

$R_\beta$ is hydrogen or alkyl;

$R_\alpha$ and $R_\beta$ together with the nitrogen atom to which they are attached may form a 3–7 membered ring which may also contain 0–2 additional N, O or S atoms; and pharmaceutically acceptable salts thereof.

This invention relates also to methods for increasing cardiac contractility using pharmaceutical compositions including an effective inotropic amount of a compound of Formula I above.

DETAILED DESCRIPTION

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

"Aralkyl" means an alkyl group substituted by an aryl radical where aryl means a phenyl or phenyl substituted with one or more substituents which may be alkyl, alkoxy, amino, nitro, carboxy, carboalkoxy, cyano, alkyl amino, halo, hydroxy, hydroxyalkyl, mercaptyl, alkyl mercaptyl, carboalkyl or carbamoyl. The preferred aralkyl groups are benzyl or phenethyl.

"Alkyl carbamoyl" means a carbamoyl group substituted by one or two alkyl groups. Preferred groups are the lower alkyl carbamoyl groups.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl, and 3-hydroxypropyl.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group as previously described substituted by an alkoxy group as previously described.

"Acyl" means an organic radical derived from an organic acid, a carboxylic acid, by the removal of its acid hydroxyl group. Preferred acyl groups are lower alkyl carboxylic acids groups such as acetyl and propionyl. Benzoyl is also preferred.

Certain of the compounds of the present invention may exist in enolic or tautomeric forms, and all of these forms are considered to be included within the scope of this invention.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

A preferred class of compounds is described by Formula I wherein z is 1 and vicinal R groups form a double bond.

Another preferred class of cardiotonic compounds of this invention is described by Formula I wherein the bicyclic ring of the molecule is represented by Formulae IIa–IIc, IIIa–IIIc or IVa–IVc, presented below:

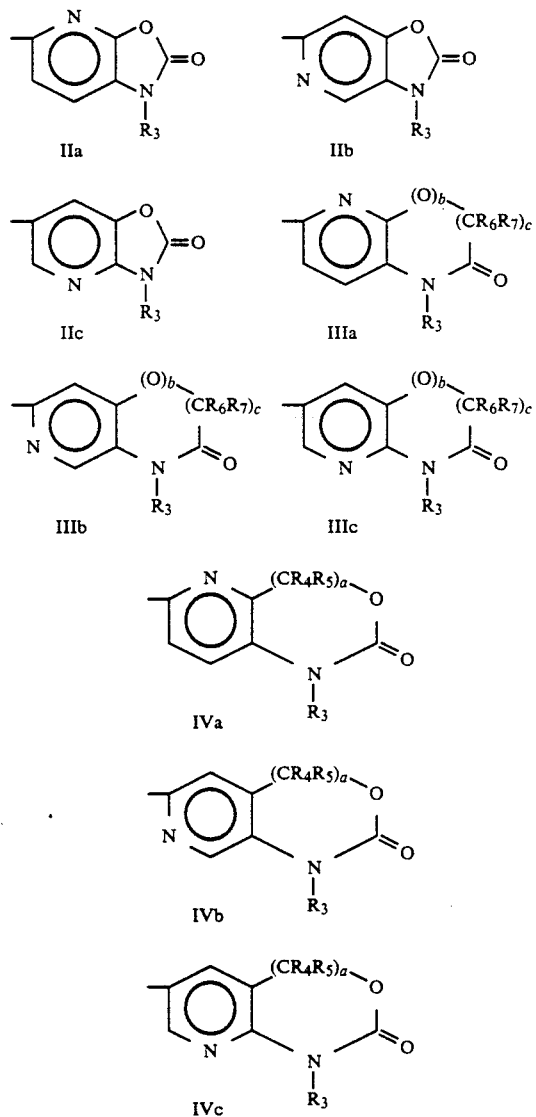

wherein:

$R_3$, $R_4$, $R_5$, $R_6$ and $R_7$ are as described above and a and c are 1 or 2.

A more preferred class of compounds are of Formulae I–IV above, wherein $R_2$ is —$(CH_2)_y$—Y and Y is of the formula —$N(R_\alpha)(R_\beta)$. Most preferred are when $R_\alpha$ and $R_\beta$ are lower alkyl and together with the nitrogen to which they are attached from a heteroring.

A further preferred class of compounds are those of Formula I, wherein $R_3$, $R_4$, $R_5$, $R_6$, $R_7$ are hydrogen or lower alkyl.

A special embodiment of the invention comprises compounds of Formula IIIc where b+c add up to 2.

A further special embodiment comprises compounds of Formula I where $R_6$ and $R_7$ form a spiro ring system, two examples of which are shown by Formula V and Va below:

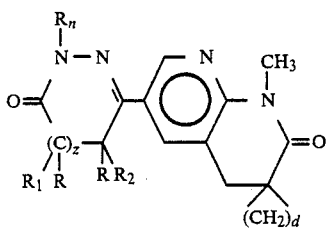

V

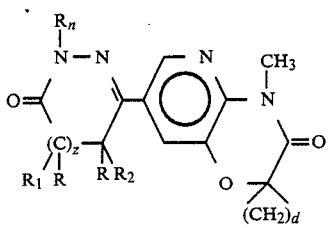

Va

Compounds of this invention may be prepared by constructing the pyridazinone or pyrazolone ring substituent on the bicyclic portion of the compound as shown below in Scheme I.

nation is a preferred reaction which occurs on the pyrido ring of the bicyclic compound in the position para to the nitrogen of the lactam. Bromination can be carried out with bromination reagents known in the art and a preferred reagent is N-bromosuccinimide. Subsequent alkylation or aralkylation of the lactam nitrogen with an appropriate alkylating agent results in the adduct of Formula VIII. Substitution of the bromo atom with a trimethylstannyl group to afford the compound of Formula IX is effected either by treatment with lithium trimethylstannate in an aprotic solvent at a temperature of about $-20°$ C. to about RT or by treatment with t-butyl lithium and trimethyltin chloride. Treatment of the stannous compound IX with a suitably substituted carboalkoxy propionyl or acetyl halide reagent in the presence of a catalyst, for example, a palladium catalyst such as $Pd(Cl)_2 (PPh_3)_2$, in an aprotic solvent such as toluene or THF, yields the corresponding alkoxycarbonyl oxo-alkyl compound X. Cyclization is accomplished by treatment with a suitable hydrazine reagent to obtain compounds of Formula I.

The preparation of preferred classes of compounds are shown in Scheme Ia below. When the keto acid derivative compound of Formula X is treated with an amine of the formula $HNR_\alpha R_\beta$ and formaldehyde, the corresponding Mannich base XI results. This may then be reacted with a hydrazine to obtain the R-substituted product. Compounds wherein Y is $-O-R_\alpha$ are pre-

SCHEME I

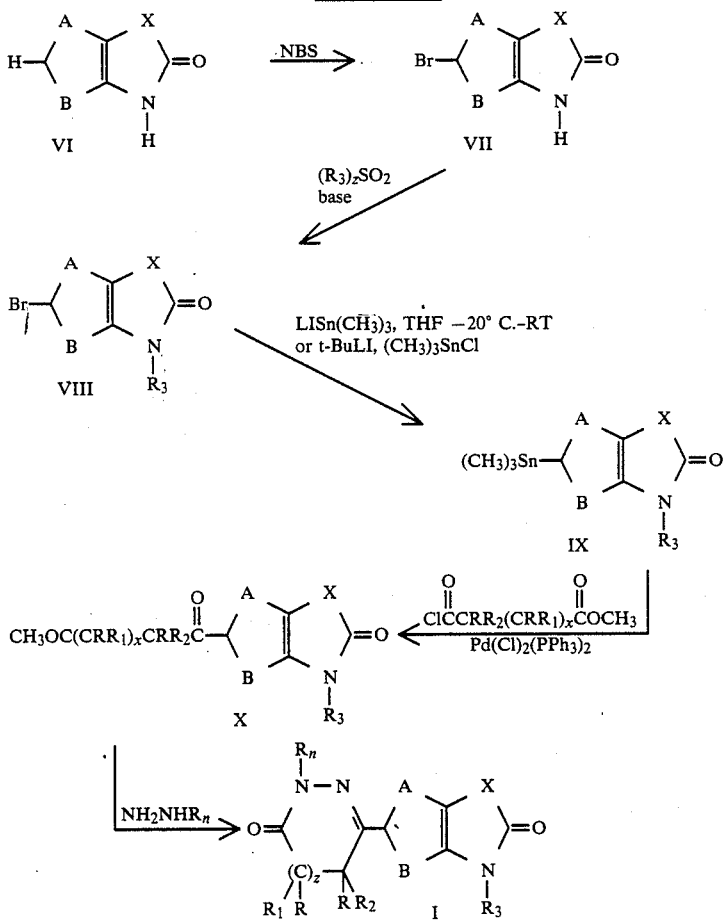

Halogeantion of a compound of Formula VI results in the corresponding halogenated Product VII. Bromipared by treating the enolate anion of X with ethylformate to generate XIII which is reduced and cyclized with hydrazine affording the desired hydroxymethylene product Ia. The corresponding thio compound can be prepared by converting the hydroxymethyl intermediate XIV into the corresponding mesylate, followed by treating the mesylate with a thiol and DBU in benzene affording the sulfide. Cyclization is accomplished with a suitable hydrazine reagent.

When the seven member-containing bicyclic ring is desired, the reaction is carried out using the halopropionate as shown below.

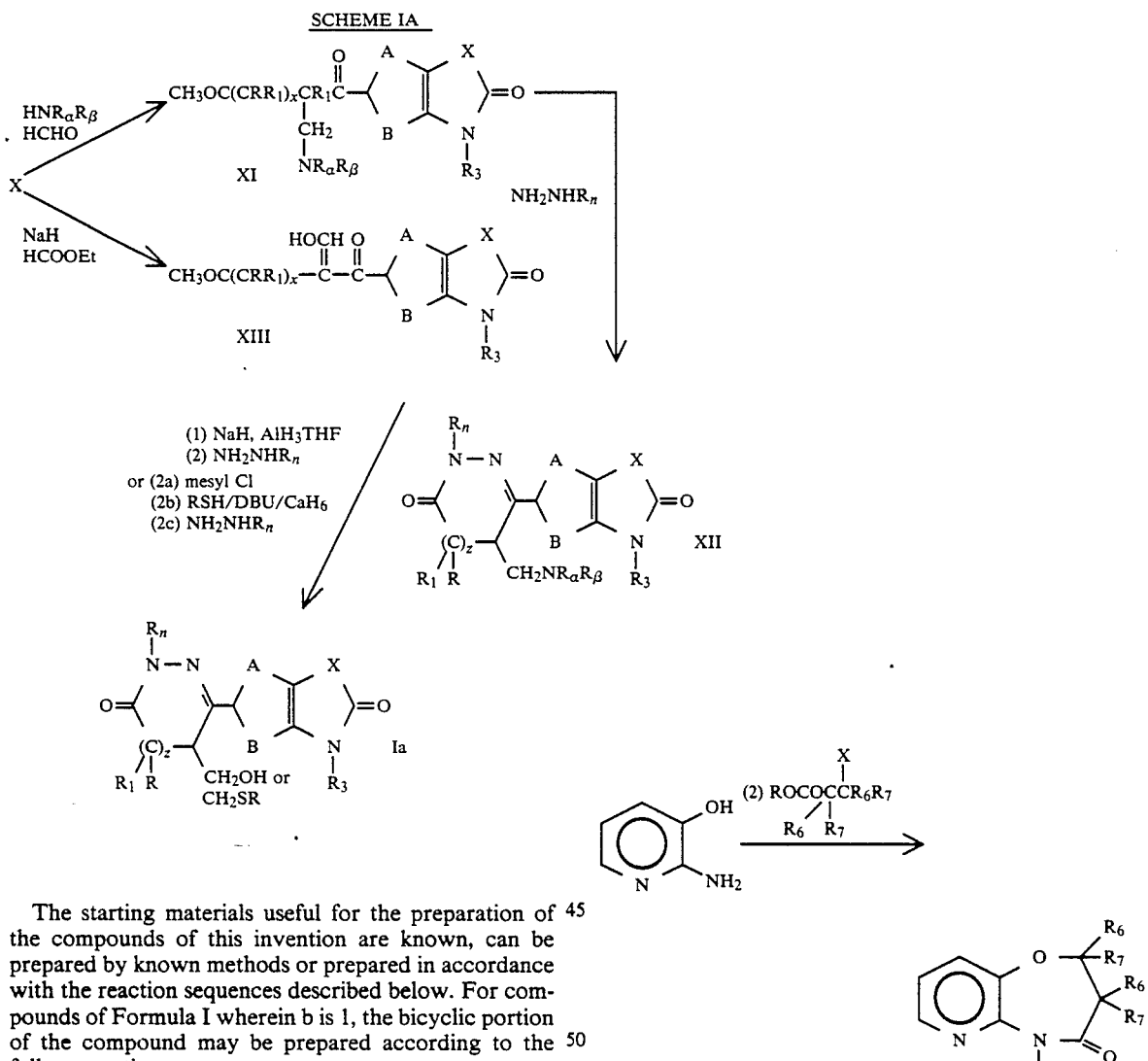

The starting materials useful for the preparation of the compounds of this invention are known, can be prepared by known methods or prepared in accordance with the reaction sequences described below. For compounds of Formula I wherein b is 1, the bicyclic portion of the compound may be prepared according to the follow reaction sequences.

When 2-amino-3-hydroxypyridine is treated with sodium hydride followed by ring closure with a α-haloacetate ester of the formula

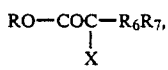

the pyridooxazinones are formed.

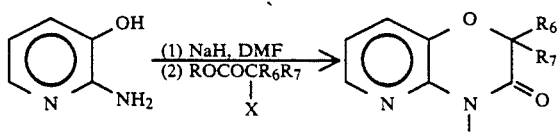

The five member-containing bicyclic ring is prepared by reacting 2- amino-3-hydroxypyridine with either phosgene or N,N-carbonyldiimidazole as shown below.

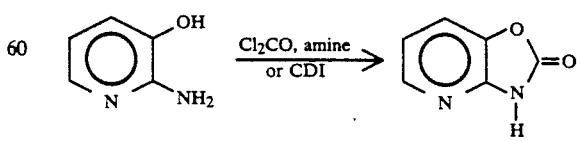

Those compounds where the oxygen atom of the pyridooxazinone ring is not directly on the pyridine ring are prepared from a 2-aminonicotinic acid or ester, reducing the latter to the corresponding alcohol and cyclizing as above. These reactions are depicted in Schemes II and IIa below.

SCHEME II

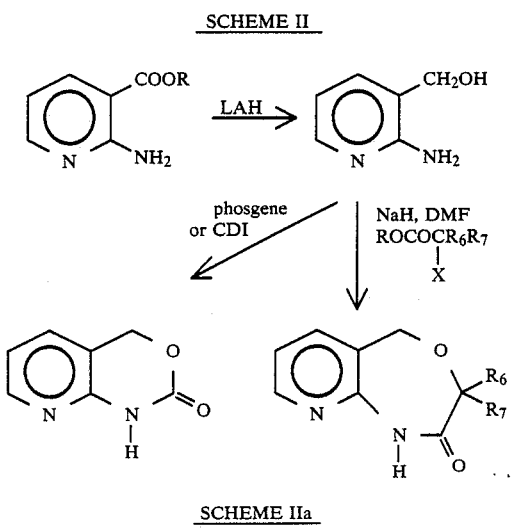

SCHEME IIa

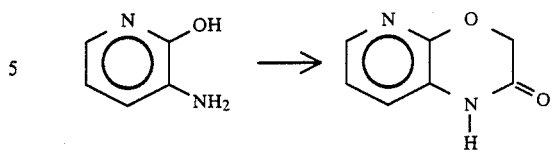

Compounds wherein $R_3$ is other than hydrogen are prepared from N-$R_3$-substituted amino-pyridines.

For compounds of Formula I wherein b is 0, the bicyclic portion of the compounds may be prepared according to one of the reaction sequences depicted in Scheme III below. Treatment of the 3-carbonyl-2-trimethylmethylamidopyridine compound depicted in Scheme III with a triphenylphosphine ylide reagent yields the unsaturated ylide addition product. The ylide chosen for the addition reaction may include R6 and R7 substituents other than hydrogen. Furthermore, the R8 substituent on the ylide determines the size of the resultant saturated ring of the bicyclic end product as shown in Scheme III. Hydrogenation of the ylide addition product and acidic cyclization to the lactam provides the bicyclic system.

SCHEME III

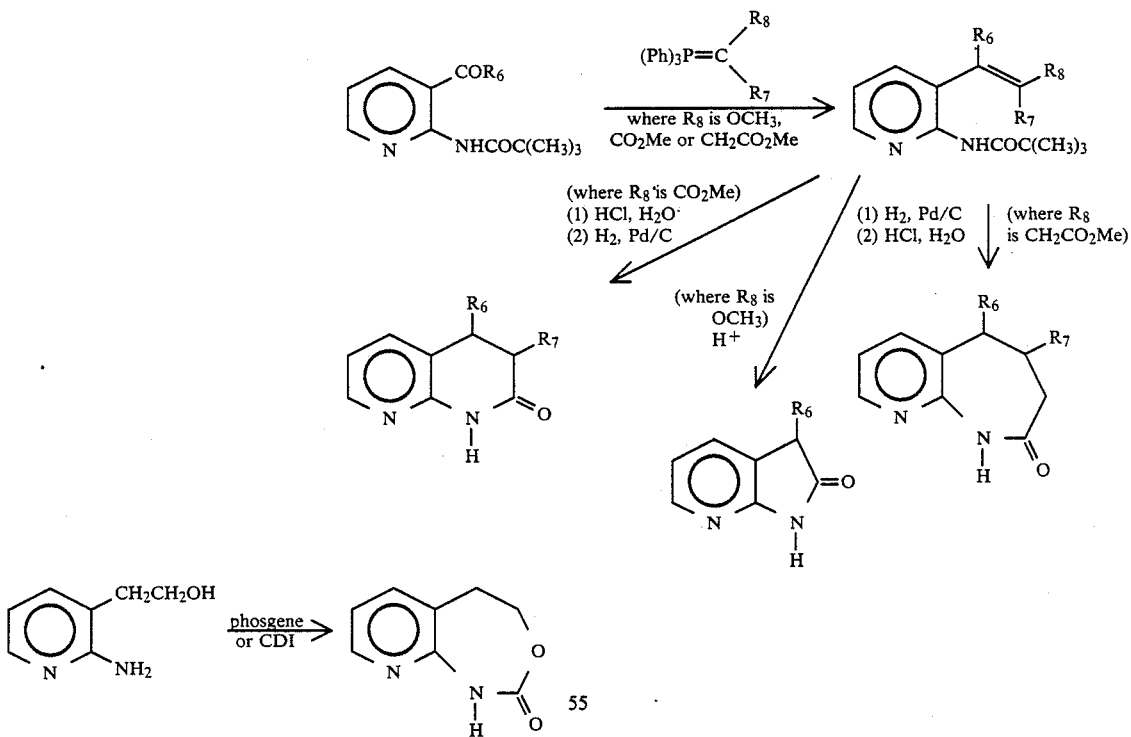

When the starting pyridine is 3-amino-4-hydroxypyridine or 2-hydroxy-3-aminopyridine then the corresponding pyridooxazinone is prepared as shown below.

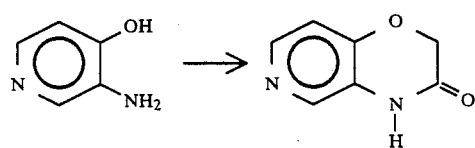

N-alkylation and halogenation of the bicyclic ring proceeds in the same manner as described for the oxygen-containing bicyclic rings discussed above.

Introduction of a spiro group into the bicyclic rings wherein the carbon atom alpha to the lactam carbonyl is unsubstituted is accomplished by reacting the intermediate compound of Formulae VIII with a strong base such as lithium diisopropyl amide and a suitable dibromoalkane such as 1,2-dibromoethane or 1,4-dibromobutane.

Specific examples of the preparation of compounds of this invention are described below.

EXAMPLE 1

THE PREPARATION OF 7-[4',5'-DIHYDRO-3'-OXO-(2H)PYRIDAZIN-6'-YL]-4-METHYL-2H-PYRIDO[3,2-b]-1,4-OXAZIN-3(4H)-ONE

Step 1. 7-Bromo-2H-pyrido[3,2-b]1,4-oxazin-3(4H)-one

To a solution of 5.6 g 2H-pyrido[3,2-b]-1,4-oxazin-3(4H)-one dissolved in 85 ml of DMF under nitrogen is added 7.96 g NBS in 50 ml of DMF. This is allowed to stir at room temperature overnight. To this is added 35 ml of water and the mixture is chilled The solid material which separates is filtered and washed with 3×100 ml $H_2O$. This is then dried under vacuum at 70° C. and then used directly in the next step.

Step 2. 7-Trimethylstannyl-2H-pyrido3,2-b]-1,4-oxazin-3-(4H)-one

A suspension of 0 24 g of 7-bromo-2H-pyrido[3,2-b]-1,4-oxazin-3(4H)-one in 14 ml THF is added dropwise to a suspension of 0.048 g sodium hydride (oil free) at room temperature. After several hours when the addition is complete about 1 ml of HMPA is added. Separately a mixture is prepared consisting of 1.5 ml of methyl lithium (1.4M) added to a solution of hexamethyltin in 5 ml THF. This is chilled to about −20° C. To this latter mixture is added the oxazinone mixture from above and allowed to stir allowing the temperature to rise to room temperature. Stirring is continued until complete. The reaction mixture is then quenched with ammonium chloride and extracted with chloroform. The combined organic layers are washed with brine, dried over sodium sulfate and evaporated to obtain a yellow solid. This material is then dissolved in chloroform and chromatographed; hexanes: ethyl acetate (75:25). The material recovered is used directly in the next step.

Step 3. 4-Methyl-7-trimethylstannyl-2H-pyrido[3,2-b]-1,4-oxazin-3(4H)-one

To a suspension of 680 mg of 7-trimethylstannyl-2H-pyrido[3,2-b]-1,4-oxazin-3(4H)-one (0.0022 mole) in 10 ml of THF is added 2.4 ml of LiN(TMS)2 (0.0024 mole) in THF. The homogenous solution is maintained under nitrogen at room temperature for 20 min , 300 mg (0.0024 mole) of dimethylsulfate sulfate is added and the reaction mixture allowed to stir overnight. The reaction mixture is then quenched with 10 ml of sat. ammonium chloride and extracted with 3×50 ml ethyl acetate. The ethyl acetate is then washed with 3×10 ml sat. ammonium chloride, dried over sodium sulfate and concentrated to obtain off white product whish is used directly in the next step.

Step 4. 4-Methyl-7-(3'-methoxycarbonyl)propionyl-2H-pyrido[3,2-b]-1,4-oxazin-3(4H)-one 650 mg (0.002 mole) of 4-methyl-7-trimethylstannyl-2H-pyrido-[3,2-b]-1,4-oxazin-3(4H)-one in 4 ml THF, 13 mg of $PdCl_2(PPh_3)_2$ and 36 mg of carbomethoxypropionyl chloride are added to an inert dried reaction vessel. This is refluxed for 22 hours; diluted with ethyl acetate and quenched with 40 ml sat. ammonium chloride. The aqueous layer is extracted with ethyl acetate and the combined organic layer washed with brine and dried over sodium sulfate. A yellow solid results on evaporation to dryness which is chromatographed using ethyl acetate:hexanes (55:45) to give the indicated product which is used directly in the next

Step 5. 7-[4',5'-Dihydro-3'-oxo-(2H)pyridazin-6'-yl]-4-methyl-2H-ovrido[3,2-b]-1,4-oxazin-3(4H)-one Hydrazine monohydrate (35 mg) is added to a solution of 4-methyl-7(3'-methoxycarbonyl)propionyl-2H-pyrido[3,2-b]-1,4-oxazin-3(4H)-one (160 mg) in 5 ml of ethanol. The reaction mixture is heated to reflux for 3 days. This is then cooled to room temperature, filtered, and upon standing the product separates M.P. 285°-290° C.

Calc'd C, 54.44; H, 4.76; N, 21.16

Found C, 54.20; H, 4.70; N, 21.13 as the quarterhydrate

EXAMPLE 2

When carbomethoxy propionyl chloride is replaced in Example 1, Step 4 with carbomethoxy-acetylchloride then the product prepared is 7-[3',4'-dihydro-3'-oxopyrazolin-5'-yl]-4-methyl-2H-pyrido[3,2-b]-1,4-oxazin-3(4H)-one.

EXAMPLE 3

When 2H-pyrido [3,2-b]-1,4-oxazin-3-(4H)-one of Example 1, Step 1 is replaced with the compounds of Table I below, then the corresponding product is obtained.

TABLE I

| |
|---|
| 2H—pyrido[3,2-b]-1,4-oxazin-3(4H)—one |
| 2H—pyrido[4,3-b]-1,4-oxazin-3(4H)—one |
| 2H—pyrido[2,3-b]-1,4-oxazin-3(4H)—one |
| 4H—pyrido[2,3-d][1,3]oxazin-2(1H)—one |
| 4H—pyrido[3,4-d][1,3]oxazin-2(1H)—one |
| 4H—pyrido[3,2-d][1,3]oxazin-2(1H)—one |
| oxazolo[4,5-b]pyridin-2(3H)—one |

EXAMPLE 4

When dimethylsulfate is replaced in Example 1, Step 3 with benzylbromide, then the corresponding 4-benzyl-7-bromo-2H- pyrido[3,2-b]-1,4-oxazin-3(4H)-one is prepared.

EXAMPLE 5

THE PREPARATION OF 7-(3'-METHOXYCARBONYL-2'-N-MORPHOLINOMETHYL)-PROPIONYL-2H-PYRIDO[3,2-b1,4-OXAZIN-3(4H)-ONE

Step 1.

A mixture of 4-methyl-7-(3'-methoxycarbonyl)- propionyl-2H-pyrido[3,2-b]-1,4-oxazin-3(4H)-one from Example 1, Step 4 (1.59 g, 5.73 mm mol.), morpholine (0.5 g) and 37% aqueous formaldehyde (0.46 g) in 3 ml of $H_2O$ is warmed at 70° C. for 3.5 hours and then at room temperature for 7 days. The aqueous mixture is extracted with chloroform and reduced in volume to generate a suspension which is filtered to give the desired product which is used directly in the next step.

Step 2.
7-[4',5'-Dihydro-5'-(N-morpholinomethyl)-3'-oxo-2H-pyridazin-6'-yl]-4-methyl-2H-pyrido3,2-b]-1,4-oxazin-3(4H)-one A solution of hydrazine monohydrate (0.17 g) and 1.14 g of 4-methyl-7-(3'-methoxycarbonyl)propionyl-2H-pyrido[3,2-b]-1,4-oxazin-3(4H)-one in 15 ml ethanol is heated to reflux for 1 day. Upon cooling the solid which precipitates is filtered to give the desired product.

EXAMPLE 6

Following the procedure of Example 5, the amines of Table II below may not be used in place of morpholine to obtain the corresponding product.

TABLE II ammonia
ethylamine
diethylamine
methylethylamine
cycolhexylamine
ethyleneimine
trimethyleneimine
piperidine
piperazine
N—methylpiperazine
N—phenylpiperazine
N—benzylpiperazine
N—methylimidazolidine
thiomorpholine
acetamide

EXAMPLE 7

When hydrazine of the foregoing examples is replaced by the substituted hydrazine of Table III below then the corresponding product is obtained

TABLE III

| | |
|---|---|
| $NH_2NHCH_3$ | $NH_2NHCONH_2$ |
| $NH_2NHCH_2CH_3$ | $NH_2NHC(=NH)NH_2$ |
| $NH_2NHCH_2Ph$ | $NH_2NHCONHSO_2$—p-tolyl |
| $NH_2NH(CH_2)_2Ph$ | $NH_2NHSO_2$—p-tolyl |
| $NH_2NHCOCH_3$ | |
| $NH_2NHCH_2CH_2OH$ | |
| $H_2NHCH_2CO_2CH_2CH_3$ | |

EXAMPLE 8

Following the procedures of the foregoing examples the following representative compounds may be prepared.

7-[4'5'-dihydro-3'-oxo-2(H)pyridazin-6'yl]-4-methyl-2H-pyrido[4,3-b]-1,4-oxazin-3(4H)-one 7-[4'5'-dihydro-3'-oxo-2(H)pyridazin-6'yl]-4-methyl-2H-pyrido[2,3-b]-1,4]oxazin-3(4H)-one 6-[4'5'-dihydro-3'-oxo-2(H)pyridazin-6'yl]-3-methyloxazolo[4,5-b]pyridin-2(3H)-one 6-[4'5'-dihydro-3'-oxo-2(H)pyridazin-6'yl]-3-methyloxazolo[4,5-c]pyridin-2(3H)-one 6-[4'5'-dihydro-3'-oxo-2(H)pyridazin-6'yl]-3-methyloxazolo[5,4-c]pyridin-2(3H)-one 6-[4'5'-dihydro-3'-oxo-2(H)pyridazin-6'yl]-1-methyl-4H-pyrido[2,3-d][1,3]oxazin-2(1H)-one 8-[4'5'-dihydro-3'-oxo-2(H)pyridazin-6'yl]-5-methyl-2,3-dihydropyrido[3,2-b][1,4]oxazepin-4(5H)-one 8-[4'5'-dihydro-3'-oxo-2(H)pyridazin-6'yl]-5-methyl-2,3-dihydropyrido[4,3-b][1,4]oxazepin-4(5H)-one 7-[4'5'-dihydro-3'-oxo-2(H)pyridazin-6'yl]-1-methyl-3,5-dihydropyrido[2,3-c]-1,4-oxazepin-2(1H)-one 7-[5'-aminomethyl-4',5'-dihydro-3'-oxo-2(H)pyridazin-6'-yl]-4-methyl-2H-pyrido[3,2-b]-1,4-oxazin-3(4H)-one 7-[5=,5'-dimethylaminomethyl-4',5'-dihydro-3'-oxo-2(H)-pyridazin-6'-yl]-4-methyl-2H-pyrido[3,2-b]-1,4-oxazin-3(4H)-one 7-[5'-(N-methylpiperazinylmethyl)-4',5'-dihydro-3'-oxo-2(H)pyridazin-6'-yl]-4-methyl-2H-pyrido[3,2-b]-1,4-oxazin-3(4H)-one 7-[5'-(N-methylpi-erdinylmethyl)-4',5'-dihydro-3'-oxo-2(H)pyridazin-6',-yl]-4-methyl-2H-pyrido[3,2-b]-1,4-oxazin-3(4H)-one 7-[5'-methoxymethyl-4',5'-dihydro-3'-oxo-2(H)-pyridazin-6'-yl]-4-methyl-2H-pyrido[3,2-b]-1,4-oxazin-3(4H)-one 7-[5'-thiomethyl-4',5'-dihydro-3'-oxo-2(H)-pyridazin-6'-yl]-4-methyl-2H-pyrido[3,2-b]-1,4-oxazin-3(4H)-one 7-[5'-methyl-4',5'-dihydro-3'-oxo-2(H)-pyridazin-6'-yl]-4-methyl-2H-pyrido[3,2-b]-1,4-oxazin-3(4H)-one 7-[2',5'-dimethyl-4',5'-dihydro3'-oxo-2(H)-pyridazin-6'-yl]-4-methyl-2H-pyrido[3,2-b]-4-oxazin-3(4H)-one 7-[4',5'-dihydro-3'-oxo-2(H)pyridazin-6'-yl]-4-ethyl-2H-pyrido[3,2-b]-1,4-oxazin-3(4H)-one 7-[4',5'-dihydro-3'-oxo-2(H)pyridazin-6'-yl]-2H-pyrido[3,2-b]-1,4-oxazin-3(4H)-one 7-[4',5'-dihydro-3'-oxo-2(H)pyridazin-6'-yl]-2,2,4-trimethyl-2H-pyrido[3,2-b]-1,4-oxazin-3(4H)-one (M.P. 226°–228° C.)

Calc'd. C, 57.96; H, 5.63; N, 19.31

Found C, 58.19; H, 5.65; N, 19.00 as the tenthhydrate 7-[4',5'-dihydro-3'-oxo-2(H)pyridazin-6'-yl]-2-methyl-2H-pyrido[3,2-b]-1,4-oxazin-3(4H)-one 7-[4',5'-dihydro-3'-oxo-2(H)pyridazin-6'-yl]-2,4-dimethyl-2H-pyrido[3,2-b]-1,4-oxazin-3(4H)-one 7-[4',5'-dihydro-3'-oxo-2(H)pyridazin-6'-yl]-2-phenyl-2H-pyrido[3,2-b]-1,4-oxazin-3(4H)-one

EXAMPLE 9

THE PREPARATION OF 6-[6-(4,5-DIHYDRO-3(2H)-3-OXOPYRIDAZINYL-1-3,4-DIHYDRO-1-METHYL-1,8-NAPHTHERIDIN-2(1H)-ONE

Step 1. 2-(pivaloylamino)pyridine

A solution of pivaloyl chloride (96 g) in methylene chloride (200 ml) is added dropwise to a cooled mixture of 2-aminopyridine (50 g) and triethylamine (108 g) in methylene chloride (650 ml). The reaction mixture is stirred overnight at RT and poured into water which is basified and the organic layer separated and concentrated in vacuo. Hexane is added to the oil which results in the precipitation of a crystalline solid which is filtered and the solid taken up in aqueous acid. The desired pyridine compound is recrystallized as a white crystalline solid.

Step 2. 3-Formyl-2-(pivaloylamino)pyridine

N-Butyl lithium (112 ml) is added dropwise to a stirred solution of the pyridine prepared according to step 1 (20 g) in THF (250 ml) at −78° C. The reaction mixture is warmed to 0° C. for about 4 hours and cooled to −78° C. Dimethyl formamide (30 ml) is added to the cooled reaction mixture and the mixture stirred overnight at RT. The reaction mixture is quenched with sat'd aqueous $NH_4Cl$ and diluted with ethyl acetate. The organic layer is separated, concentrated and treated with aqueous acid. The aqueous layer is washed with ethyl acetate, brought to a neutral pH and extracted with ethyl acetate. The organic extract is dried, concentrated in vacuo and cooled, resulting in the formation of a crystalline material which is further purified on a silica gel column to afford a white crystalline solid used in the next step.

Step 3.
3-(2-Carbomethoxyvinyl)-2-(pivalovlamino)-pyridine

A solution of the formyl compound of step 2. above (9.8 g) in methylene chloride (100 ml) is added dropwise to a solution of carbomethoxymethylide triphenylphosphine (16 g) in methylene chloride (125 ml). The reaction mixture is stirred at reflux overnight, cooled to RT, concentrated in vacuo and petroleum ether added. The ethereal solution is cooled resulting in the precipitation of the desired material as a white crystalline solid, M.P 148°–150° C.

Step 4. Dihydro-1.8-naphtheridin-2(1H)-one

A solution of the carbomethoxy vinyl compound of step 3. above (9 g), 10% Pd on C in ethanol (400 ml) is introduced into a Parr apparatus and stirred under hydrogen until the reaction is complete. The reaction mixture is filtered, the filtrate concentrated in vacuo, and the residue dissolved in 6N HCl and stirred at 110° C. overnight. The reaction mixture is neutralized, extracted with chloroform and dried, filtered and concentrated in vacuo. The resulting solid is chromatographed on silica gel resulting in a purified white crystalline product, M.P. 160°–162° C.

Step 5.
6-Bromo-3.4-dihydro-1.8-naphtheridin-2(1H)-one

A solution of N-bromo succinimide (3.7 g) in dimethyl formamide (70 ml) is added dropwise to a stirring solution of the naphtheridine of step 4. above maintained at about −10° C. The reaction mixture is warmed to RT and stirred overnight. Water is added to the mixture and the resulting suspension is stirred for 15 min., filtered, the filtered solid washed with water and recrystallized from DMF to yield the desired product as a white crystalline solid.

Step 6.
3,4-Dihydro-6-trimethylstannyl-1.8-naphtheridin-2(1H)-one

A solution of 6-bromo-3,4-dihydro-1,8-naphtheridin-2(1H)-one (0.25g) in a mixture of HMPA (0.4ml) and THF (5ml) is added to a suspension of sodium hydride (0.03g) in THF (3ml) and stirred under nitrogen at RT for about 90 min. The resulting solution of the sodium salt is added dropwise to a solution of lithium trimethylstannate (2.4mmole) in THF (5ml) at −20° C. and the reaction mixture stirred under nitrogen at −20° C. for 4 hours and at RT overnight. The mixture is diluted with ethyl acetate, washed with aqueous sodium bicarbonate, the organic layer is separated, dried and concentrated in vacuo giving a crystalline solid which is chromatographed on silica gel affording the desired product as an off white crystalline solid.

Step 7.
3,4-Dihydro-1-methyl-6-trimethylstannyl-1.8-naphtheridin-2(1H)-one

Lithium bistrimethylsilylamide (0.9 ml) is added to a solution of the tin compound of step 6 above (0.2 g) in THF (10 ml) and the reaction mixture stirred at 0° C. for about 45 min. Dimethyl sulfate (0.1 g) is added to the mixture which is stirred at RT overnight under nitrogen. The reaction is quenched with sat'd aqueous NH4Cl and diluted with ethyl acetate. The organic layer is separated, washed with sat'd aqueous NH4Cl, water and brine, dried and concentrated in vacuo affording a crystalline solid. The solid is chromatographed on silica gel yielding the desired product as a white crystalline solid.

Step 8.
6-(3-Carbomethoxypropionoyl)-3,4-Dihydro-1-methyl-1,8-naphtheridin-2(1H)-one 2-Carbomethoxypropionoyl chloride (0.06 g) is added to a mixture of the tin compound of step 7. above (0.1 g) and bistriphenylphosphine palladium chloride (0.01 g) in benzene (5 ml). The reaction mixture is stirred under nitrogen at 90° C. overnight, cooled to RT, methylene chloride added, and washed with sat'd aqueous sodium bicarbonate solution. The organic layer is dried, concentrated in vacuo and chromatographed on silica gel affording the desired product as a crystalline solid, M.P. 106°–108° C.

Step 9.
6-[6-(4,5-dihydro-3(2H)-3oxo-pyridazinyl]-3,4-dihydro-1-methyl-1,8-naphtheridin-2(1H)-one Hydrazine hydrate (13 ml) is added to the carbomethoxy compound of step 8. above (0.25 g) in absolute ethanol (8 ml)and the reaction mixture stirred at reflux overnight. The mixture is cooled in an ice bath and the precipitate is filtered and dried in vacuo affording the desired product as a crystalline solid, M.P.=276°–278° C.

(Cal'd: C 59.42; H 5.56; N 21.32)
(Found: C 59.77; H 5.50; N 21.56).

The compounds of Formula I possess positive inotropic activity and are useful as cardiotonic agents in the treatment of humans and other mammals for cardiac disorders including congestive heart failure. The effectiveness of the compounds of this invention a inotropic agents may be determined by the following pharmacologic tests which evaluate the change in cardiac contractile force upon exposure to a dose of said compounds. The ganglionic-beta blocked anesthetized dog procedure is one such standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flowis monitored using a precalibrated, noncanulating electro-magnetic flow probe positioned around the thoracic aorta. Heart rate is monitored using a cardiotachometer triggered by the QRS complex of the limb lead II EKG. The right femoral vein is cannulatd for intravenous infusion of drugs. Body temperature is maintained at 37° C.

Following a 30 min postsurgical stabilization period, control valves are recorded. Myocardial depression is induced by ganglionic and beta receptor blockade. Initially, the responsiveness of the autonomic nervous systems is assessed by performing a 30 sec bilateral carotid occlusion (BCO). Ten minutes later, a saline solution of isoproterenol 0.3 mg/kg, i.v. is administered to assess beta receptor integrity. Ten minutes after that, a saline solution of mecamylamine 2 mg/kg, i.v. is infused, followed by a saline solution of propranolol 1 mg/kg, i.v. plus 0.3 mg/kg/hr. Twenty minutes later, a second BCO is performed to demonstrate ganglionic blockade followed by a second injection of saline isoproterenol 0.3 mg/kg, i.v. to demonstrate beta blockade. Ten minutes later, the test compound or vehicle is administered intravenously in ascending doses at 30 min intervals at 1.5 ml/min in a total volume of 3.5 ml. On completion of the experiment, both BCO and isoproterenol challenges are repeated to verify ganglionic and beta blockade.

The results of the blocked dog test show that compounds of the present invention increase contractile force and heart rate, and aortic blood flow in a dose related manner while maintaining arterial pressure.

Additional test procedures which have been found to be an efficient means for ascertaining the inotropic activity of the compounds of this invention are described below.

Guinea Pig Atria Inotropic Screening Concentrations

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66 and $CaCl_2$, 1.25 gassed with a mixture of 95% $O_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 2-gauge silver wire wound into a tight coil approximately 12-14 mm in diameter. Electrodes are connected to a Grass stimulator via Grass constant current unit. Tissues are driven at 90 pulses per minute with 5 msec duration at current levels 20% greater than threshold for continuous beat.

Cumulative concentrations of test drugs are added to the tissue bath at intervals sufficient to allow developed tension to peak at a new level.

The increase in developed tension is each tissue for each compound concentration is measured, and the results are averaged and used to construct cumulative concentrationresponse curves. Slopes for these regressions calculated via the method of Finney (1971) are compared using Student's t-test.

The following in vitro method is another means for measuring the inotropic potency of the present compounds. This method is a modification of the enzyme inhibition method reported by Thompson and Appleman (1970) and Thompson et al. (1974), and is believed to correlate to in vivo inotropic activity in humans.

Inhibition of Peak III cAMP Phosphodiesterase Activity

The test compounds are included in media comprising a radioactivity labeled substrate ($^3$H-cyclic nucleotide) such as adenosine 3':5'-monophosphate (cyclic AMP) and quanine-3': 5'-nucleotidease isolate from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ion exchange resin so that it is not quantitated with the liquid scintillation counter.

Anesthetized Dog Procedure

Male mongrel dogs are anesthetized with pentobarbital (35 mg/kg, i.v.) and intubated. Femoral artery and veins I5 are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.0-18.5 kg) are anesthetized with sodium pentobarbital (35 mg/kg, i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluidfilled catheters are filled with heparinized 50% dextrose solution, and the chest is closed and evacuated.

The dog is trained and acclimated to its environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl; sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response.

Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such a patient should be effective to achieve and maintain the desired therapeutic response.

We claim:

1. A compound of the formula

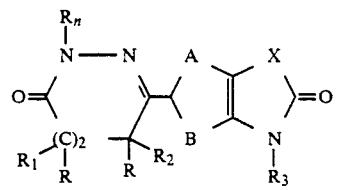

wherein
A is —C= or —N=;
B is —C=C—, —C=N— or —N=C—;
provided that A or B represents a nitrogen-containing group;
X is —(CR$_4$R$_5$)$_a$—(O)$_b$—(CR$_6$R$_7$)$_c$—;
a and c are 0, 1 or 2;
b and z are 0 or 1;
provided that a+b+c=1,
R$_n$ is hydrogen, alkyl, aralkyl, aryl, acyl, carbalkoxy, carbamyl, carbalkoxyalkyl, hydroxyalkyl, alkoxyalkyl, or amidino;
R, R$_1$, R$_2$, R$_3$, R$_5$ and R$_6$ are hydrogen, alkyl, or aralkyl;
R$_4$ is hydrogen, alkyl, aryl, or aralkyl;
R$_7$ is hydrogen, alkyl, aralkyl, aryl, acyl, carbalkoxy, carbalkoxyalkyl, hydroxyalkyl, alkoxyalkyl, amidino, alkoxy, amino, nitro, carboxy, cyano, alkyl amino, halo, hydroxy, mercaptyl, alkyl mercaptyl, carboalkyl or carbamoyl;
R and groups on vicinal carbon atoms may together form a carbon-carbon double bond provided that R$_n$ is hydrogen and z=1;
R$_6$ and R$_7$ geminal groups may together form a spiro substituent, —(CH$_2$)$_d$—, where d is 2 to 5;
R$_2$ is hydrogen or —(CH$_2$)$_y$—Y where y is 1–3;
Y is hydrogen, —O—R$_\alpha$, —S—R$_\alpha$ or —NR$_\alpha$R$_\beta$;
R$_\alpha$ is hydrogen, alkyl or acyl;
R$_\beta$ is hydrogen or alkyl;
R$_\alpha$ and R$_\beta$ together with the nitrogen atom to which they are attached may form a 3–7 membered ring which may also contain 0–2 additional N, O or S atoms; or a pharmaceutically acceptable salt thereof.

2. A compound according to claim 1 where b is 1.
3. A compound according to claim 1 where b is 0.
4. A compound according to claim 2 or 3 where
A is —C=;
B is —C=N—; and a or c is 0.

5. A compound according to claim 2 or 3 where
A is —C≡;
B is —N=C—; and
a is 0.

6. A compound according to claim 2 or 3 where
A is —N≡;
B is —C=C—; an
a is 0.

7. A compound according to claim 2 where
A is —C≡;
B is —C=N—; and
a and c are 0.

8. A compound according to claim 4 where $R_2$ is hydrogen or —$(CH_2)_y$—Y where y is 1-3 and Y is hydrogen.

9. A compound according to claim 4 where $R_2$ is —$CH_2$—$NR_\alpha R_\beta$, where $R_\alpha$ and $R_\beta$ are hydrogen or alkyl.

10. A compound according to claim 4 where $R_2$ is —$CH_2$-$NR_\alpha R_\beta$, where $R_\alpha$ and $R_\beta$ taken together form a 3-7 membered ring which may also contain 0-2 additional N, O or S atoms.

11. A compound according to claim 10 where $R_{60}$ and $R_\beta$ are alkylene and taken together with the nitrogen to which they are attached form a 3-7 member azacyclic ring.

12. A compound according to claim 10 where $R_\alpha$ and $R_\beta$ taken together with the nitrogen to which they are attached form a six member ring which may also contain one additional N or O atom.

13. A compound according to claim 12 where the six member ring is selected from the group of N-piperazinyl, N-morpholino and N-piperidinyl.

14. A compound according to claim 4 where R groups on vicinal carbon atoms together form a carbon-carbon double bond and $R_n$ is hydrogen.

15. A compound according to claim 1 which is 6-[4',5'-dihydro-3'-oxo-2(H)pyridazin-6'-yl]-3-methyloxazolo-[4,5-b]pyridin-2(3H)-one or a pharmaceutically acceptable salt thereof.

16. A compound according to claim 3 whre A is —C≡; and B

17. A compound according to claim 4 wherein b is 0 and $R_6$ and $R_7$ together form a spiro substituent.

18. A compound according to claim 3 where $R_3$ is alkyl or aralkyl.

19. A pharmaceutical composition comprising an effective inotropic amount of a compound according to claim 1 in admixture with a pharmaceutical carrier.

20. A method for increasing carditonic contractility in a patient requiring such treatment which comprises administering to such patient an effective amount of a compound according to claim 1.

* * * * *